United States Patent
Satoh et al.

(10) Patent No.: US 9,636,358 B2
(45) Date of Patent: May 2, 2017

(54) METHOD AND DEVICE FOR PRODUCING HYDROGEN CONTAINING FLUID

(71) Applicant: MiZ Company Limited, Kanagawa (JP)

(72) Inventors: Fumitake Satoh, Kanagawa (JP); Ryousuke Kurokawa, Kanagawa (JP); Bunpei Satoh, Kanagawa (JP)

(73) Assignee: MIZ COMPANY LIMITED, Kamakura-shi, Kanagawa (JP)

( * ) Notice: Subject to any disclaimer, the term of this patent is extended or adjusted under 35 U.S.C. 154(b) by 0 days.

(21) Appl. No.: 14/891,851

(22) PCT Filed: Mar. 13, 2015

(86) PCT No.: PCT/JP2015/057553
§ 371 (c)(1),
(2) Date: Nov. 17, 2015

(87) PCT Pub. No.: WO2015/137499
PCT Pub. Date: Sep. 17, 2015

(65) Prior Publication Data
US 2016/0089394 A1   Mar. 31, 2016

(30) Foreign Application Priority Data

Mar. 13, 2014  (JP) .................................. 2014-050115
Nov. 7, 2014   (JP) .................................. 2014-227296

(51) Int. Cl.
*A61K 33/00*   (2006.01)
*B01D 53/22*   (2006.01)
(Continued)

(52) U.S. Cl.
CPC ............. *A61K 33/00* (2013.01); *B01D 53/22* (2013.01); *C01B 3/06* (2013.01); *C01B 3/10* (2013.01); *Y02E 60/36* (2013.01)

(58) Field of Classification Search
CPC ............... B01D 53/22; B01D 2256/16; B01D 2257/108; A61K 33/00; B65D 77/03;
(Continued)

(56) References Cited

U.S. PATENT DOCUMENTS 3,419,400 A * 12/1968 Hayhurst ............... B65D 81/18
                                                              206/205
4,437,567 A   3/1984 Jeng
(Continued)

FOREIGN PATENT DOCUMENTS

CN   101932297 A   12/2010
CN   102803156 A   11/2012
(Continued)

OTHER PUBLICATIONS

Chinese Office Action (Issuance Date: May 12, 2016) of corresponding Application No. 201580000856.1 of pp. 1-6.
(Continued)

*Primary Examiner* — Jason M Greene
(74) *Attorney, Agent, or Firm* — Muncy, Geissler, Olds & Lowe, P.C.

(57) ABSTRACT

A device for producing a hydrogen containing fluid, having a container that stores fluid which able to be used for a living organism and has water vapor permeability, a hydrogen generating system that generates hydrogen by using moisture, and a wrapping member that encloses the container and the hydrogen generating system and has low hydrogen molecule permeability. The wrapping member encloses the container and the hydrogen generating system located outside the container, and a treatment to increase humidity in a space between an outer surface of the container and an inner surface of the wrapping member is performed.

18 Claims, 1 Drawing Sheet

(51) Int. Cl.
*C01B 3/06* (2006.01)
*C01B 3/10* (2006.01)

(58) Field of Classification Search
CPC .... B65D 77/04; B65D 81/18; B65D 81/2069; B65D 2565/387; B65D 2565/388; A23L 3/3409; A23L 3/34095; A01N 1/02; A01N 1/0231; C01B 3/06; C01B 3/10
See application file for complete search history.

(56) References Cited

U.S. PATENT DOCUMENTS

| | | | |
|---|---|---|---|
| 4,857,409 A * | 8/1989 | Hazelton | B29C 47/0023 428/35.2 |
| 5,624,794 A * | 4/1997 | Bitensky | A01N 1/02 435/2 |
| 5,789,151 A * | 8/1998 | Bitensky | A01N 1/02 435/2 |
| 6,877,601 B1 * | 4/2005 | Colombo | A23L 3/3409 206/213.1 |
| 2004/0067182 A1 * | 4/2004 | Kelly | A23L 3/3409 422/305 |
| 2005/0121399 A1 * | 6/2005 | Hayashi | A61K 33/00 210/749 |
| 2006/0120945 A1 * | 6/2006 | Warner | A23L 3/34095 423/477 |
| 2007/0122577 A1 | 5/2007 | Iwasaki et al. | |
| 2007/0148256 A1 * | 6/2007 | Yanagihara | A61K 33/00 424/600 |
| 2008/0078404 A1 * | 4/2008 | Martens | A61M 16/04 128/207.15 |
| 2011/0111048 A1 | 5/2011 | Satoh et al. | |
| 2012/0245540 A1 | 9/2012 | Zimnitsky et al. | |
| 2012/0263629 A1 * | 10/2012 | Satoh | C01B 3/08 422/162 |
| 2013/0098250 A1 | 4/2013 | Satoh et al. | |
| 2013/0112600 A1 | 5/2013 | Satoh et al. | |
| 2013/0245540 A1 | 9/2013 | Satoh et al. | |
| 2014/0010483 A1 * | 1/2014 | Shih | B65D 31/02 383/105 |
| 2015/0069056 A1 * | 3/2015 | Kishimoto | B65D 77/04 220/23.87 |

FOREIGN PATENT DOCUMENTS

| | | |
|---|---|---|
| EP | 2407141 A1 | 1/2012 |
| EP | 2508484 A1 | 10/2012 |
| EP | 2508485 A1 | 10/2012 |
| EP | 2522633 A1 | 11/2012 |
| JP | 4486157 | 6/2010 |
| JP | 2011177242 | 9/2011 |
| TW | 200526734 A | 8/2005 |
| TW | 201032794 A | 9/2010 |
| WO | WO 2010103894 | 9/2010 |
| WO | WO 2012056923 | 5/2012 |

OTHER PUBLICATIONS

Taiwan Office Action (Issuance Date: May 12, 2016) of corresponding Application No. 10520587910 of pp. 1-6.
European Search Report (Issuance Date May 30, 2016) of corresponding Application No. 15760863.9 of pp. 1-7.

* cited by examiner

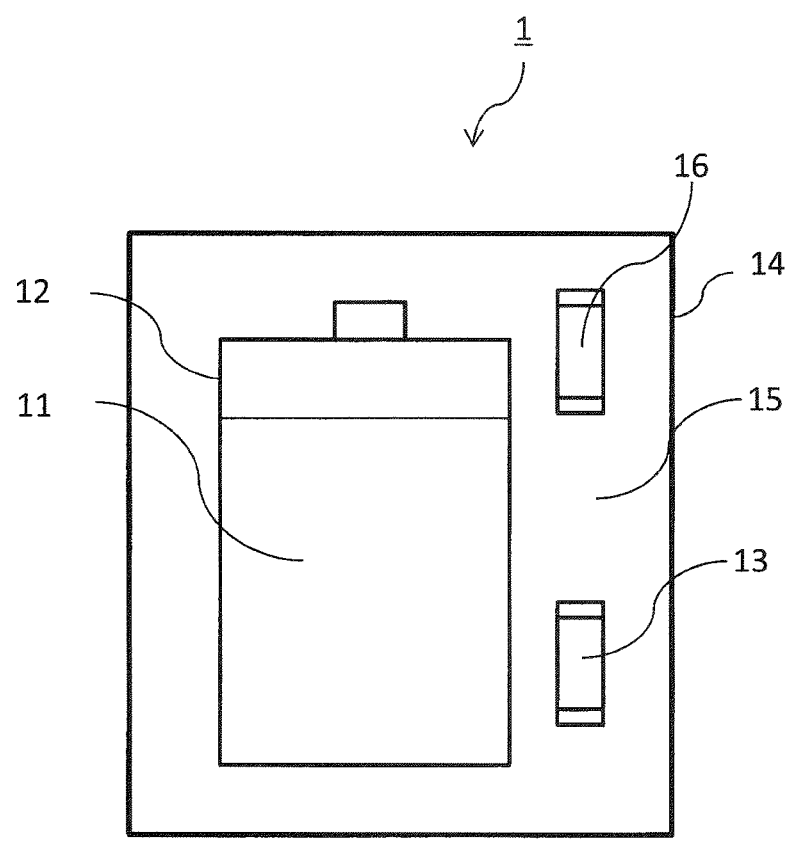

METHOD AND DEVICE FOR PRODUCING HYDROGEN CONTAINING FLUID

TECHNICAL FIELD

The present invention relates to a method and to a device for producing a hydrogen containing fluid which is abele to be used for (or applicable to, suitable for) a living organism.

BACKGROUND ART

As a prior art, there has been known a nondestructive method for including hydrogen molecules in fluid which is able to be used for a living organism. This method comprises: preparing the fluid stored in a container, such as a plastic bag, which has high hydrogen molecule permeability; storing the fluid together with the container in a portable hydrogen storage having low hydrogen molecule permeability; filling the hydrogen storage with a liquid or gas, such as hydrogen containing water, which contains hydrogen molecules, thereby to include hydrogen molecules in the fluid without opening the container. It is said that, according to this method, hydrogen molecules are dissolved in the fluid while being barriered by the hydrogen storage having low hydrogen molecule permeability, so that the hydrogen molecules are less likely to disappear into the external air even during the delivery and storage processes.

PRIOR ART DOCUMENT

Patent Document

[Patent Document 1] JP Patent No. 4486157

SUMMARY OF INVENTION

Problems to be solved by Invention

However, even though the hydrogen storage has low hydrogen molecule permeability, it may not be avoided that the hydrogen molecules steadily decreases during the delivery and storage processes because hydrogen molecules are the smallest molecules. This may make it difficult to industrially produce a hydrogen containing fluid which is able to be used for a living organism.

Problems to be solved by the present invention include providing a method and a device for producing a hydrogen containing fluid in which hydrogen molecules do not substantially decrease even during the delivery and storage processes.

Means for Solving Problems

The present invention solves the above problems through providing a device for producing a hydrogen containing fluid as a hydrogen molecule supplying type. The device comprises: a container that stores fluid which is able to be used for a living organism and has water vapor permeability; a hydrogen generating system that generates hydrogen by using moisture (tiny drops of water in the air); and a wrapping member that encloses the container and the hydrogen generating system and has low hydrogen molecule permeability. The wrapping member encloses the container and the hydrogen generating system located outside the container. A treatment to increase humidity in a space between an outer surface of the container and an inner surface of the wrapping member is performed.

According to another aspect of the present invention, the above problems are solved through providing a method for producing a hydrogen containing fluid. The method comprises: providing a container having water vapor permeability in which fluid is stored, the fluid being able to be used for a living organism; enclosing the container and a hydrogen generating system located outside the container in a wrapping member having low hydrogen molecule pet ineability; increasing humidity in a space between an outer surface of the container and an inner surface of the wrapping member; and transmitting hydrogen molecules generated by the hydrogen generating system from an exterior of the container into the fluid.

Effect Of Invention

According to the present invention, a specific configuration can be obtained in which hydrogen molecules steadily increase rather than decreasing during the delivery and storage processes. This allows industrial production of a hydrogen containing fluid which is designed such that the hydrogen concentration is optimized when the fluid is delivered to end users.

BRIEF DESCRIPTION OF DRAWING(S)

The sole FIGURE is a front elevational view illustrating a device for producing a hydrogen containing fluid (as a hydrogen molecule supply type) according to an embodiment of the present invention.

MODE(S) FOR CARRYING OUT THE INVENTION

Embodiments of the present invention will be described hereinafter. The sole figure is a front elevational view illustrating a device 1 as a hydrogen molecule supply type according to an embodiment of the present invention, and the example shown in the figure is used to describe a device for producing hydrogen containing fluid which is abele to be used for a living organism according to the present invention. This example of a device 1 comprises: a container 12 that stores fluid 11 which is able to be used for a living organism (hereinafter called as 'a living organism applicable fluid 11') and has water vapor permeability; a hydrogen generating system 13 that generates hydrogen by using moisture, i.e. tiny drops of water in the air; and a wrapping member 14 that encloses the container 12 and the hydrogen generating system 13 (stores and seals the container 12 and the hydrogen generating system 13) and has low hydrogen molecule permeability. The hydrogen molecule supply type device 1 as an embodiment of the present invention is obtained through: locating the hydrogen generating system 13 outside the container 12 which stores the living organism applicable fluid 11 and has water vapor permeability; enclosing the hydrogen generating system 13 and the container 12 in the wrapping member 14 having low hydrogen molecule permeability; and performing a treatment to increase humidity in a space between an outer surface of the container 12 and an inner surface of the wrapping member 14.

Examples of the living organism applicable fluid 11 include: normal saline solution prepared in terms of osmolality for use as injection, intravenous drip, transfusion, and the like; liquid for injection and oral liquid for supply of water, nutrition, electrolytes, and the like; liquid for injection and normal saline solution in which a medical agent is dissolved; liquid medical agent; blood preparation (blood for blood transfusion) and own blood to be used for blood transfusion; enteral solution; and drinking water. Examples of the living organism applicable fluid 11 may further include: organ preservative solution prepared to preserve organs; cell culture liquid; cell maintenance liquid; living organism applicable fluid including lymph cells and vaccines used in cancer immune therapy, vaccine therapy, and similar therapies; peritoneal dialysis solution; dialysis solution; and myocardial protective medicine. The living organism applicable fluid 11 of the present embodiment refers to a concept that represents general fluids to be applied orally or parenterally to living organisms for improvement in maintaining vital functions and prevention, treatment or the like of diseases and disorders.

By including hydrogen molecules in such a living organism applicable fluid 11, it is possible to add functions of hydrogen molecules for living organisms, such as, but not limited to, an action of inhibiting oxidative stress, to the functions possessed originally by the living organism applicable fluid.

Diseases and disorders that can fall within the applicable region of the living organism applicable fluid 11 in which hydrogen is contained include, but are not limited to, liver damage due to chemicals or harmful substances; ischemic reperfusion disorder; circulatory system diseases such as arteriosclerosis; digestive system diseases, such as gastric ulcer and gastric mucosal disorder; respiratory diseases; complications from diabetes (e.g., high blood pressure, cerebral infarction, myocardial infarction, etc.); renal diseases; cataract; skin diseases; various inflammatory diseases; neurological disorders; cancer; and oxidative stress diseases, such as aging, attributable to free radicals or lipid peroxide. In particular, the living organism applicable fluid in which hydrogen is contained may be suitably applied to diseases related to acute oxidative stress, such as ischemic reperfusion disorder.

A certain amount of hydrogen molecules may be preliminarily contained in the living organism applicable fluid 11 prior to the application of the present invention. In this case, according to the present invention, hydrogen molecules can be supplied to the living organism applicable fluid 11 thereby to continuously maintain the concentration of dissolved hydrogen.

The container to be preferably used as the container 12 having water vapor permeability may be, but is not limited to, a plastic container made of a material, such as polyethylene, polypropylene, polyethylene terephthalate, and polystyrene, used for an infusion solution bag or intravenous bag. The water vapor transmission rate ($g/m^2$/day (40° C., 90% RH)) of the container 12 having water vapor permeability may be 0.001 or more, preferably 0.01 or more, more preferably 0.1 or more, more preferably 0.5 or more, and more preferably 1 or more.

In the present invention, hydrogen molecules are transmitted from a exterior of the container 12 having water vapor permeability so that the hydrogen molecules transfer into the living organism applicable fluid 11. Therefore, the container 12 having water vapor permeability may not have to be preliminarily opened. However, the present invention does not exclude cases in which hydrogen molecules are transmitted in the opened state.

The living organism applicable fluid 11 stored in the container 12 having water vapor permeability may be commercially available after the outside of the container 12 has already been covered by some kind of one or more exterior bags. Even in such a case, the present invention can be carried out if the exterior bag or bags have water vapor permeability. In the present invention, therefore, the concept of "the living organism applicable fluid 11 stored in the container 12 having water vapor permeability" encompasses cases in which the container 12 is duplicated or multiplicated such as by one or more exterior bags, provided that the exterior bags have water vapor permeability.

The hydrogen generating system 13 includes an agent that reacts with humidity (water vapor) to generate hydrogen, and if necessary may further include additives, such as an appropriate hydrogen generating reaction promoter that promotes the hydrogen generation reaction. Examples of the hydrogen generating agent include, but are not limited to, a metal having a higher ionization tendency than that of hydrogen, and hydrogenated compounds including a metal hydride. In consideration of good reactivity with humidity, metal calcium, calcium hydride, metal magnesium, magnesium hydride, and the like may preferably be used. In consideration of the safety of reaction product and other factors, metal magnesium, metal aluminum, metal zinc, metal nickel, metal cobalt, and the like may also be preferably used.

Examples of the hydrogen generating reaction promoter include a pH adjuster for adjusting pH to that suitable for promoting the reaction of the hydrogen generating agent with humidity (moisture). Examples of such a pH adjuster include substances that supply hydrogen ions (H+), such as citric acid, adipic acid, malic acid, acetic acid, succinic acid, gluconic acid, lactic acid, phosphoric acid, hydrochloric acid, sulfuric acid, and cation-exchange resin. When an amphoteric metal, such as aluminum and zinc, is used as the hydrogen generating agent, an alkaline agent, such as calcium hydroxide, calcium oxide, and anion-exchange resin, can also be used other than the above acids. Among them, calcium hydroxide (hydrated lime), burnt lime (calcium oxide), calcined calcium, magnesium oxide, magnesium hydroxide, anion-exchange resin, and the like may preferably be used.

Examples of the hydrogen generating reaction promoter also include a hygroscopic agent and a drying agent because such agents absorb humidity to promote the hydrogen generation reaction. Examples of the hygroscopic agent and drying agent include, but are not limited to, the above-described ion-exchange resins, deliquescent substances such as calcium chloride, and substances that adsorb water at the porous surface, such as aluminum oxide. When the hydrogen generating agent is placed directly in contact with the container having water vapor permeability, the container may possibly be damaged due to the reaction heat. It is therefore preferred that the hydrogen generating system 13, which includes the hydrogen generating agent, is treated with a heat protection treatment by being covered by a nonwoven fabric, gas permeable film, and the like.

It can be said that a wrapping member to be preferably used as the wrapping member 14 having low hydrogen molecule permeability has a property that, even after the wrapping member filled fully or almost fully with normal saline solution is immersed for 5 hours in a hydrogen dissolved water which is stably maintained at about the saturated concentration (1.6 ppm under a water temperature of 20° C. and 1 atmosphere) and has a volume of 20 times the internal volume of the container, the concentration of dissolved hydrogen in the normal saline solution only comes to 100 ppb or less, preferably 10 ppb or less, and particularly preferably 1 ppb or less. Examples of such a wrapping member 14 include, but are not limited to, wrapping members having gas barrier properties, including those using aluminum, such as an aluminum foil wrapping member and an aluminum foil-laminated film.

In the hydrogen molecule supply-type exterior body 1 of the present invention, water vapor originated from the living organism applicable fluid 11 can permeate the container 12 having water vapor permeability to initiate the reaction in the hydrogen generating system 13. In the present invention, however, it is enough if hydrogen gas is generated at least by the chemical reaction of the hydrogen generating system 13 with the water vapor originated from the living organism applicable fluid 11 which has permeated the container 12. Therefore, water may be forcibly supplied in a subsidiary manner or in any other appropriate manner such as by dropping water drops on the hydrogen generating system 13 before enclosing the hydrogen generating system 13 in the wrapping member 14.

In particular, in the hydrogen molecule supply-type exterior body 1 of the present embodiment and the method for producing a living organism applicable fluid in which hydrogen is contained using the same, a "treatment to increase humidity" in a space 15 between the container 12 and the wrapping member 14 may be performed thereby to further increase the hydrogen molecules dissolved in the living organism applicable fluid 11. Such a "treatment to increase humidity" may include, but is not limited to, a process to reduce the volume of the space 15 between the container 12 and the wrapping member 14 such as by evacuating the gas which occupies the space 15 between the container 12 and the wrapping member 14. The "treatment to increase humidity" may also include, but is not limited to, a process to maintain the container 12 enclosed in the wrapping member 14 at a temperature higher than a room temperature for a certain period of time (preferably for 10 minutes or longer) thereby to increase the amount of water vapor permeating the container 12 into the living organism applicable fluid 11. Examples of a temperature higher than a room temperature as referred to herein include a temperature that is not lower than 20° C. which is the "standard temperature" for storing medicines, preferably not lower than 25° C. which is the "upper limit of ordinary temperature," more preferably not lower than 30° C. which is the "upper limit of room temperature," and further preferably not lower than 40° C. which is the "upper limit of lukewarm temperature." Gas existing in the space between the container 12 and the wrapping member 14 is air if the working environment for enclosing the container 12 and the hydrogen generating system 13 in the wrapping member 14 is an air environment, but the gas is not limited to air and may also be an inert gas, such as nitrogen gas and argon gas.

The amount of the hydrogen generating agent to be used in the hydrogen generating system 13 can be determined with reference to the criteria as below. The present inventors have found that, in the living organism applicable fluid 11 in which hydrogen is contained obtained according to the present invention, the degree of decrease in the concentration of dissolved hydrogen is smaller in some samples compared with other samples after the living organism applicable fluid 11 in which hydrogen is contained is taken out together with the bag (container 12) from the hydrogen molecule supply-type exterior body 1, even though the concentration is the same at the time of production.

After intensively studying the reason for the above, the present inventors have discovered the followings. First, the amount of the hydrogen generating agent used in the hydrogen generating system 13 relates to the above event. Second, the hydrogen generating agent is not necessarily sufficient if only used with a calculated amount required for hydrogen molecules to be saturated in the amount (so-called volume) of the living organism applicable fluid 11 stored in the container 12 having water vapor permeability. Third, it is preferred to further use an amount of the hydrogen generating agent enough for the spatial volume (so-called extra volume) of an upper space in the container 12 to be substituted by hydrogen molecules.

For example, saturating normal saline solution in a bag of 500 mL volume with dissolved hydrogen under ordinary temperature/ordinary pressure (20° C., 1 atmosphere) requires at least 0.4 mmol of hydrogen molecules (1.6 mg/L (solubility of hydrogen molecules)×0.5L=0.8 mg=0.4 mmol). If metal calcium is used as the hydrogen generating agent in this instance, at least 0.4 mmol=40.078×0.4=16.0312 mg of calcium is necessary in reference to the chemical reaction formula of metal calcium with water: $Ca+2H_2O \rightarrow Ca(OH)_2+H_2$. If, however, the bag (container 12) has an extra volume of 150 mL, the fully filled volume as the sum of the volume and the extra volume is 650 mL, so 1.6 mg/L×0.65L=1.04 mg=0.52 mmol can be obtained in accordance with the above calculation, i.e., 0.52 mmol=40.078×0.52=20.84056 mg. It is therefore preferred that the hydrogen generating agent is used with an amount of 20.84056 mg or more.

More in general, the substance quantity (mmol) of the hydrogen generating agent to be used in the hydrogen generating system 13 of the present invention is preferably not less than a value of (1.6 (mg/L)×(the fully filled volume (L) of the container 12 having water vapor permeability and storing the living organism applicable fluid 11)/2)×((coefficient of the hydrogen generating agent in the left-hand side of the reaction formula of the hydrogen generating agent with water)/(coefficient of the hydrogen molecule in the right-hand side of the reaction formula of the hydrogen generating agent with water)), and may be more preferably not less than twice that value, more preferably not less than five times that value, and more preferably not less than ten times that value, in consideration of the margin.

There is a method as below, as a means for non-destructively determining whether hydrogen molecules are actually generated from the hydrogen generating system 13 reacting with humidity in the hydrogen molecule supply-type exterior body 1 of the present invention without opening the container 12 having water vapor permeability to measure the concentration of dissolved hydrogen in the living organism applicable fluid 11 stored in the container.

That is a method of including a hydrogen molecule indicator in the hydrogen molecule supply-type exterior body 1, as illustrated in the sole figure. The hydrogen molecule indicator includes an oxidation-reduction indicator and a hydrogen molecule catalyst that are stored in a transparent or semitransparent second container 16 having hydrogen molecule permeability. The hydrogen molecule catalyst may be noble metal colloid (such as platinum colloid and palladium colloid) or the like. According to this method, hydrogen molecules generated from the hydrogen generating system 13 permeate the transparent or semitransparent second container 16 having hydrogen molecule permeability to react with the hydrogen molecule indicator, thereby changing the color of the oxidation-reduction indicator, and the generation of hydrogen molecules can thus be visually confirmed. If the second container 16 is selected to have the same hydrogen molecule permeability as that of the container 12 which stores the living organism applicable fluid 11, not only the generation of hydrogen molecules can be confirmed, but the degree of permeation of hydrogen molecules into the living organism applicable fluid 11 can also be verified.

For example, although not limited thereto, when a hydrogen molecule indicator is used which includes methylene blue as the oxidation-reduction indicator and platinum colloid as the hydrogen molecule catalyst, hydrogen molecules are activated by the platinum colloid thereby to reduce the methylene blue of oxidative type so that the blue solution becomes clear. Therefore, by confirming whether the hydrogen molecule indicator becomes clear when opening the hydrogen molecule supply-type exterior body 1, it can be nondisruptively determined whether hydrogen molecules have been generated in the space 15 surrounded by the wrapping member 14 having low hydrogen molecule permeability and accordingly whether hydrogen molecules have permeated into the living organism applicable fluid 11.

If the blue color of the methylene blue is not clear, it can be determined that hydrogen molecules are not generated from the hydrogen generating agent due to some trouble or that the generated hydrogen molecules have got out of the hydrogen molecule supply-type exterior body 1.

In order to obtain sufficient effects for living organisms, the concentration of dissolved hydrogen in the living organism applicable fluid in which hydrogen is contained may be 0.01 mg/L or more, preferably 0.05 mg/L or more, more preferably 0.1 mg/L or more, still more preferably 0.2 mg/L or more, yet more preferably 0.4 mg/L or more, further preferably 0.6 mg/L or more, still further preferably 0.8 mg/L or more, and yet further preferably 1.0 mg/L or more, when the fluid is used under a water temperature of 20° C. and 1 atm.

EXAMPLES

Working examples of the present invention will be described hereinafter. The dissolved hydrogen meter used for measuring the concentration of dissolved hydrogen in the living organism applicable fluid 11 is a DH meter available from DKK-Toa Corporation (main body type "DHDI-1," electrode (probe) type "HE-5321," transponder type "DHM-F2").

Example 1

An infusion solution bag of polyethylene storing 500 mL of normal saline solution ("Japanese Pharmacopoeia normal saline solution OTSUKA NORMAL SALINE" available from Otsuka Pharmaceutical Co., Ltd., hereinafter denoted by reference numeral 12 because the infusion solution bag corresponds to the container 12 storing the living organism applicable fluid 11 of the present invention), and a hydrogen generating system 13 of the present invention obtained by wrapping 0.5 g of metal calcium ("CALCIUM" available from KANTO CHEMICAL CO., INC.) with a nonwoven fabric, were enclosed in an aluminum bag ("MZ-05" available from HAGIOS CORPORATION (mudazero.net), hereinafter denoted by reference numeral 14 because the aluminum bag corresponds to the wrapping member 14 of the present invention), and thereafter the aluminum bag 14 was heat-sealed using a vacuum sealer ("VP-300" available from Takato Technica Co., Ltd.) while decreasing the volume of a space 15 between the infusion solution bag 12 and the aluminum bag 14 at −0.1 MPa.

Three samples were produced in the same manner and left in a room (room temperature: 20° C.). One of them was opened 24 hours later, the second was opened 36 hours later, and the third was opened 3 weeks later. The concentration of dissolved hydrogen in each normal saline solution (hereinafter denoted by reference numeral 11 because the normal saline solution corresponds to the living organism applicable fluid 11 of the present invention) was measured using the DH meter.

Example 2

An infusion solution bag 12 of polyethylene storing 500 mL of normal saline solution ("Japanese Pharmacopoeia normal saline solution OTSUKA NORMAL SALINE" available from Otsuka Pharmaceutical Co., Ltd.), and a hydrogen generating system 13 of the present invention obtained by wrapping 0.5 g of metal calcium ("CALCIUM" available from KANTO CHEMICAL CO., INC.) with a nonwoven fabric, were enclosed in an aluminum bag 14 ("MZ-05" available from HAGIOS CORPORATION), and thereafter the aluminum bag 14 was heat-sealed using a vacuum sealer ("VP-300" available from Takato Technica Co., Ltd.) while decreasing the volume of a space 15 between the infusion solution bag 12 and the aluminum bag 14 at −0.1 MPa. The aluminum bag 14 was then left in a constant temperature/humidity chamber ("LU-113" available from ESPEC CORP., chamber temperature: 60° C.) to be maintained in an environment of a temperature higher than the room temperature. After 48 hours, the aluminum bag 14 was put out from the constant temperature/humidity chamber, and the concentration of dissolved hydrogen in the normal saline solution 11 was measured using the DH meter.

Example 3

A peritoneal dialysis solution bag 12 of polypropylene covered at the outside by an external bag of polypropylene and storing 2,000 mL of peritoneal dialysis solution ("MIDPELIQ L135" available from TERUMO CORPORATION), and a hydrogen generating system 13 of the present invention obtained by wrapping 3 g of metal calcium ("CALCIUM" available from KANTO CHEMICAL CO., INC.) with a nonwoven fabric, were enclosed in an aluminum bag 14 ("MZ-05" available from HAGIOS CORPORATION), and thereafter the aluminum bag 14 was heat-sealed using a vacuum sealer ("VP-300" available from Takato Technica Co., Ltd.) while decreasing the volume of a space 15 between the peritoneal dialysis solution bag 12 and the aluminum bag 14 at −0.1 MPa. The aluminum bag 14 was then left in a constant temperature/humidity chamber ("LU-113" available from ESPEC CORP., chamber temperature: 60° C.) to be maintained in an environment of a temperature higher than the room temperature. After 5 days, the aluminum bag 14 was put out from the constant temperature/humidity chamber, and the concentration of dissolved hydrogen in the peritoneal dialysis solution 11 was measured using the DH meter.

Comparative Example 1

An infusion solution bag 12 of polyethylene storing 500 mL of normal saline solution ("Japanese Phatinacopoeia normal saline solution OTSUKA NORMAL SALINE" available from Otsuka Pharmaceutical Co., Ltd.), and 0.5 g of metal calcium ("CALCIUM" available from KANTO CHEMICAL CO., INC.) wrapped with a nonwoven fabric, were enclosed in an aluminum bag 14 ("MZ-05" available from HAGIOS CORPORATION), and thereafter the aluminum bag 14 was heat-sealed without vacuuming.

Three samples were produced in the same manner and left in a room (room temperature: 20° C.). One of them was opened 24 hours later, the second was opened 36 hours later, and the third was opened 3 weeks later. The concentration of dissolved hydrogen in each normal saline solution 11 was measured using the DH meter.

Reference Example 1

An infusion solution bag 12 of polyethylene storing 500 mL of normal saline solution ("Japanese Pharmacopoeia normal saline solution OTSUKA NORMAL SALINE" available from Otsuka Pharmaceutical Co., Ltd.) was enclosed in an aluminum bag 14 ("MZ-05" available from HAGIOS CORPORATION), and thereafter the aluminum bag 14 was filled with hydrogen dissolved water of a saturation concentration of 1.6 mg/L as substitute for the hydrogen generating system 13 and heat-sealed.

Two samples were produced in the same manner and left in a room (room temperature: 20° C.). One of them was opened 24 hours later, and the other was opened 36 hours later. The concentration of dissolved hydrogen in each normal saline solution 11 was measured using the DH meter.

Results (concentration of dissolved hydrogen DH (mg/L) of Examples 1 to 3, Comparative Example 1, and Reference Example 1 are listed in Table 1.

TABLE 1

|  | 24 hrs later | 36 hrs later | 48 hrs later | 5 days later | 3 weeks later |
|---|---|---|---|---|---|
| Example 1 | 0.06 | 0.13 | — | — | 0.77 |
| Example 2 | — | — | 1.15 | — | — |
| Example 3 | — | — | — | 1.10 | — |
| Comparative Example 1 | 0.03 | 0.04 | — | — | 0.29 |
| Reference Example 1 | 0.55 | 0.53 | — | — | — |

Example 4

An infusion solution bag 12 of polyethylene storing 500 mL of normal saline solution ("Japanese Pharmacopoeia normal saline solution OTSUKA NORMAL SALINE" available from Otsuka Pharmaceutical Co., Ltd.), and a hydrogen generating system 13 of the present invention obtained by wrapping 0.4 g of metal magnesium ("MAGNESIUM POWDER Mg100" available from Kanto Metal Corporation) and 0.2 g of cation-exchange resin ("DIAION FMK10" available from Mitsubishi Chemical Corporation) with a nonwoven fabric, were enclosed in an aluminum bag 14 ("MZ-05" available from HAGIOS CORPORATION), and thereafter the aluminum bag 14 was heat-sealed using a vacuum sealer ("VP-300" available from Takato Technica Co., Ltd.) while decreasing the volume of a space 15 between the infusion solution bag 12 and the aluminum bag 14 at −0.1 MPa.

Two samples were produced in the same manner and left in a room (room temperature: 20° C.). One of them was opened 24 hours later, and the other was opened 36 hours later. The concentration of dissolved hydrogen in each normal saline solution 11 was measured using the DH meter.

Example 5

An infusion solution bag 12 of polyethylene storing 500 mL of normal saline solution ("Japanese Pharmacopoeia normal saline solution OTSUKA NORMAL SALINE" available from Otsuka Pharmaceutical Co., Ltd.), and a hydrogen generating system 13 of the present invention obtained by wrapping 0.5 g of calcium hydride ("CALCIUM HYDRIDE" available from Wako Pure Chemical Industries, Ltd.) with a nonwoven fabric, were enclosed in an aluminum bag 14 ("MZ-05" available from HAGIOS CORPORATION), and thereafter the aluminum bag 14 was heat-sealed using a vacuum sealer ("VP-300" available from Takato Technica Co., Ltd.) while decreasing the volume of a space 15 between the infusion solution bag 12 and the aluminum bag 14 at −0.1 MPa.

Two samples were produced in the same manner and left in a room (room temperature: 20° C.). One of them was opened 24 hours later, and the other was opened 36 hours later. The concentration of dissolved hydrogen in each normal saline solution 11 was measured using the DH meter.

Example 6

An infusion solution bag 12 of polyethylene storing 500 mL of normal saline solution ("Japanese Pharmacopoeia normal saline solution OTSUKA NORMAL SALINE" available from Otsuka Pharmaceutical Co., Ltd.), and a hydrogen generating system 13 of the present invention obtained by wrapping 0.4 g of metal aluminum ("ALUMINUM POWDER" available from MINALCO LTD.), 0.2 g of cation-exchange resin (identified above), and 0.1 g of calcium chloride ("CALCIUM CHLORIDE" available from Wako Pure Chemical Industries, Ltd.) with a nonwoven fabric, were enclosed in an aluminum bag 14 ("MZ-05" available from HAGIOS CORPORATION), and thereafter the aluminum bag 14 was heat-sealed using a vacuum sealer ("VP-300" available from Takato Technica Co., Ltd.) while decreasing the volume of a space 15 between the infusion solution bag 12 and the aluminum bag 14 at −0.1 MPa.

Two samples were produced in the same manner and left in a constant temperature/humidity chamber ("LU-113" available from ESPEC CORP., chamber temperature: 40° C.) to be maintained in an environment of a temperature higher than the room temperature. One of them was taken out 24 hours later and the other was taken out 36 hours later from the constant temperature/humidity chamber. The concentration of dissolved hydrogen in each normal saline solution 11 was measured using the DH meter.

Example 7

An infusion solution bag 12 of polyethylene storing 500 mL of normal saline solution ("Japanese Pharmacopoeia normal saline solution OTSUKA NORMAL SALINE" available from Otsuka Pharmaceutical Co., Ltd.), and a hydrogen generating system 13 of the present invention obtained by wrapping 0.4 g of metal aluminum (identified above), 0.15 g of calcium hydroxide ("CALCIUM HYDROXIDE" available from Wako Pure Chemical Industries, Ltd.), and 0.1 g of calcium chloride (identified above) with a nonwoven fabric, were enclosed in an aluminum bag 14 ("MZ-05" available from HAGIOS CORPORATION), and thereafter the aluminum bag 14 was heat-sealed using a vacuum sealer ("VP-300" available from Takato Technica Co., Ltd.) while decreasing the volume of a space 15 between the infusion solution bag 12 and the aluminum bag 14 at −0.1 MPa.

Two samples were produced in the same manner and left in a constant temperature/humidity chamber ("LU-113" available from ESPEC CORP., chamber temperature: 40° C.) to be maintained in an environment of a temperature higher than the room temperature. One of them was taken out 24 hours later and the other was taken out 36 hours later from the constant temperature/humidity chamber. The concentration of dissolved hydrogen in each normal saline solution 11 was measured using the DH meter.

Results (concentration of dissolved hydrogen DH (mg/L) of Examples 4 to 7 are listed in Table 2.

TABLE 2

|  | 24 hrs later | 36 hrs later |
|---|---|---|
| Example 4 | <0.01 | 0.02 |
| Example 5 | 0.30 | 0.45 |
| Example 6 | 0.04 | 0.11 |
| Example 7 | 0.10 | 0.16 |

[Consideration]

It has been confirmed from the results of Examples 1 to 3 and Comparative Example 1 that vacuuming the space 15 between the container 12 and the wrapping member 14 as in Examples 1 to 3 allows the concentration of dissolved hydrogen DH to increase from 0.06 mg/L of 24 hours later until 3 weeks later. It has also been confirmed that, in contrast to the above, in the Comparative Example without vacuuming the space 15 between the container 12 and the wrapping member 14, the concentration of dissolved hydrogen DH of 24 hours later is a low value of 0.03 mg/L, and the concentration of dissolved hydrogen DH of 3 weeks later is only 0.29 mg/L, which shows a significant difference in increase compared with 0.77 mg/L of Example 1.

It has been confirmed that, even in the cases of Examples 4 to 7 in which metal magnesium, calcium hydride, or metal aluminum rather than metal calcium is used as the hydrogen generating system 13, the concentration of dissolved hydrogen DH of 36 hours later tends to increase from the concentration of dissolved hydrogen DH of 24 hours later, as in the above Examples 1 to 3.

DESCRIPTION OF REFERENCE NUMERALS

1 . . . Hydrogen molecule supply-type exterior body
11 . . . Living organism applicable fluid
12 . . . Container
13 . . . Hydrogen generating system
14 . . . Wrapping member
15 . . . Space
16 . . . Second container

The invention claimed is:

1. A method for producing a hydrogen containing fluid, comprising:
providing a container having water vapor permeability in which fluid is stored, the fluid being able to be used for a living organism;
enclosing the container and a hydrogen generating system located outside the container in a wrapping member having low hydrogen molecule permeability;
increasing humidity in a space between an outer surface of the container and an inner surface of the wrapping member, said increasing humidity including maintaining the container enclosed in the wrapping member in an environment of a temperature higher than a room temperature for a predetermined period of time; and
transmitting hydrogen molecules generated by the hydrogen generating system from an exterior of the container into the fluid.

2. The method according to claim 1, wherein the temperature higher than a room temperature is 30° C. or higher.

3. A method for producing a hydrogen containing fluid, comprising:
providing a container having water vapor permeability in which fluid is stored, the fluid being able to be used for a living organism;
enclosing the container and a hydrogen generating system located outside the container in a wrapping member having low hydrogen molecule permeability;
increasing humidity in a space between an outer surface of the container and an inner surface of the wrapping member, said increasing humidity including reducing a volume of a space between the outer surface of the container and the inner surface of the wrapping member; and
transmitting hydrogen molecules generated by the hydrogen generating system from an exterior of the container into the fluid,
wherein the transmitting hydrogen molecules step is performed until a concentration of dissolved hydrogen in the fluid comes to 1 mg/L or more.

4. A device for producing a hydrogen containing fluid, comprising:
a container that stores fluid which is able to be used for a living organism and has water vapor permeability;
a hydrogen generating system that generates hydrogen by using moisture and/or liquid water;
a wrapping member that encloses the container and the hydrogen generating system and has low hydrogen molecule permeability; and
a hydrogen molecule indicator that is enclosed in the wrapping member together with the container and the hydrogen generating system,
wherein the wrapping member encloses the container and the hydrogen generating system located outside the container, and a treatment to increase humidity in a space between an outer surface of the container and an inner surface of the wrapping member is performed, and
wherein the hydrogen molecule indicator includes an oxidation-reduction indicator and a hydrogen molecule catalyst that are stored in a transparent or semitransparent container having hydrogen molecule permeability.

5. The device according to claim 4, wherein the oxidation-reduction indicator and the hydrogen molecule catalyst are methylene blue and platinum colloid.

6. The method according to claim 1, wherein the transmitting hydrogen molecules step is performed until a concentration of dissolved hydrogen in the fluid comes to 0.01 mg/L or more.

7. The method according to claim 6, wherein the transmitting hydrogen molecules step is performed until a concentration of dissolved hydrogen in the fluid comes to 1mg/L or more.

8. A method for producing a hydrogen containing fluid, comprising:
providing a container having water vapor permeability in which fluid is stored, the fluid being able to be used for a living organism;
enclosing the container and a hydrogen generating system located outside the container in a wrapping member having low hydrogen molecule permeability;
increasing humidity in a space between an outer surface of the container and an inner surface of the wrapping member, said increasing humidity including reducing a volume of a space between the outer surface of the container and the inner surface of the wrapping member; and transmitting hydrogen molecules generated by the hydrogen generating system from an exterior of the container into the fluid, wherein the wrapping member is made of an aluminum foil or an aluminum foil-laminated film having gas barrier properties.

9. The method according to claim 3, wherein the hydrogen generating system includes at least either a metal hydride or a metal that has a higher ionization tendency than that of hydrogen.

10. The method according to claim 9, wherein the metal having a higher ionization tendency than that of hydrogen is metal calcium.

11. The method according to claim 3, wherein the hydrogen generating system further includes a hydrogen generating reaction promoter.

12. The method according to claim 3, wherein the hydrogen generating system is further treated with a heat protection treatment.

13. The method according to claim 12, wherein the heat protection treatment is a heat protection treatment of being covered with a nonwoven fabric.

14. The method according to claim 8, wherein the hydrogen generating system includes at least either a metal hydride or a metal that has a higher ionization tendency than that of hydrogen.

15. The method according to claim 14, wherein the metal having a higher ionization tendency than that of hydrogen is metal calcium.

16. The method according to claim 8, wherein the hydrogen generating system further includes a hydrogen generating reaction promoter.

17. The method according to claim 8, wherein the hydrogen generating system is further treated with a heat protection treatment.

18. The method according to claim 12, wherein the heat protection treatment is a heat protection treatment of being covered with a nonwoven fabric.

* * * * *